United States Patent [19]

Globus

[11] Patent Number: 4,601,817

[45] Date of Patent: Jul. 22, 1986

[54] TREATMENT OF HAZARDOUS MATERIALS

[76] Inventor: Alfred R. Globus, 26-53 210th St., Bayside, N.Y. 11360

[21] Appl. No.: 652,898

[22] Filed: Sep. 21, 1984

[51] Int. Cl.[4] .......... C10G 17/00; C07C 1/20

[52] U.S. Cl. .......... 208/262; 585/469; 585/638; 210/716; 210/909

[58] Field of Search .......... 208/262; 585/469, 638; 210/716, 723, 909

[56] References Cited

U.S. PATENT DOCUMENTS

| | | | |
|---|---|---|---|
| 4,379,746 | 4/1983 | Norman et al. | 208/262 |
| 4,379,752 | 4/1983 | Norman | 210/712 |

OTHER PUBLICATIONS

Pytlewski et al., Treatment of Hazardous Waste Symp. (1980), U.S. EPA, Off. Res. & Dev., pp. 72-76.

Chem. Abs., 82, 1975, 89831k.

*Primary Examiner*—Curtis R. Davis

*Attorney, Agent, or Firm*—Evelyn M. Sommer

[57] ABSTRACT

Process for removing chlorinated hydrocarbons such as ethylene dibromide and PCBs from a material containing the same such as a fuel, hazardous waste material, fuel containing a hazardous waste material, which comprises forming a ternary alloy of sodium, copper and lead by dispersing sodium metal in oil and reacting the same with a catalytic amount of copper and at least the same amount of lead to provide a slurry of said alloy; contacting the material containing the halogenated hydrocarbon with said slurry using an amount of alloy whereby the sodium is present in excess with respect to halogen present; carrying out said contacting at a temperature of about 250°-300° F. under intense mixing and separately recovering the sodium halide, copper-lead and unreacted sodium-copper-lead alloy from the substantially halogen free material.

The invention also contemplates as novel the ternary alloy of Na, Cu and Pb and the oil slurry containing the same.

9 Claims, No Drawings

TREATMENT OF HAZARDOUS MATERIALS

This invention relates to a process for management of hazardous materials and namely polychlorinated biphenyls (PCBs) as found in fuels, textile dyes, printing inks, paints, carbonless copy paper, fireproofing agents, electrical capacitors, electrical insulation, transformer fluids, hydraulic systems, heat exchangers, hazardous wastes, and the like. More particularly this invention relates to a process for assuring protection against and specifically elimination of the potential health effects of polychlorinated biphenyls in the wide range of materials noted above, but particularly in so-called toxic wastes or hazardous waste materials and even more particularly in the hazardous wastes used as fuels or the fuels per se.

BACKGROUND

The Polychlorinated Biphenyls (PCBs) were commercially introduced in 1930 for various industrial applications in this country. The properties of chemical and thermal stability, non-flammability and electrical insulation were ideally suited for a host of electrical, hydraulic, plasticizer and other end uses. By 1970, yearly U.S. production reached a peak of 38.5 million kilograms (84.9 million pounds). The Monsanto Corporation was the largest domestic producer of PCB which sold the material under the trade name Aroclor.

In 1968, rice-bran oil processed in Japan, accidentally became contaminated with large quantities of Japanese-made PCB. Approximately 1000 people of all ages were poisoned by consuming the contaminated oil. Symptoms of the PCB ingestion became known as "Yusho" disease and catalyzed widespread interest in PCB contamination in food products and the environment.

As a result of the "Yusho" incident, the Food and Drug Administration (FDA) initiated a survey to determine the extent and levels to which PCB might enter the food chain. Because of the large quantities of PCB in use and the chemical and thermal stability, PCB was identified in numerous classes of food products and packaging materials. The ubiquitous nature of PCB contamination in surface waters was showing up in the food chain. In 1972, the FDA established temporary tolerances for PCB in several classes of foods, and issued a final order reducing these tolerances in 1979.

The Toxic Substances Control Act of 1976 (TSCA) authorizes the Environmental Protection Agency to obtain production and test data from industry on selected chemical substances and mixtures, and to regulate the substances when needed. Section 6 (e) of TSCA prohibits all manufacture, processing, distribution in commerce and use of PCBs after July 1, 1979. In addition, section 6 (e) requires the EPA to promulgate rules prescribing marking and disposal of PCBs by July 1, 1977. The TSCA PCB ban and 1977 regulations were intended to protect the environment from further contamination of PCBs by stopping new manufacture and usage, and controlling existing PCBs.

The EPA promulgated regulations under 40 CFR Part 761, published in the Federal Register of May 31, 1979 (44 FR 31514) to implement section 6 (e) of TSCA.

By definition, the EPA encompassed all PCB contaminated substances in two categories: PCB liquids and non-liquid PCBs. Anything contaminated with PCBs at a level of 50 ppm or greater became included in the regulations. The intent of such a broad definition was to include numerous non-electrical items such as PCB contaminated rags, debris, containers, pipes, valves, fuels, etc., which had potential for introducing PCBs into the environment. PCB liquids and non-liquid PCBs between 50 and 500 ppm could be disposed of by landfill or incineration. Any PCB liquids greater than 500 ppm could only be disposed of by incineration. Landfill of PCBs at high concentration (500 ppm) was considered environmentally unsound practice because of the risk of eventually escaping into the environment. Other non-liquid PCBs (500 ppm) such as transformers, 55 gallon drums, process equipment, etc., could be drained, solvent washed and tested to insure PCB levels were less than 500 ppm prior to disposal in a landfill. After Mar. 1, 1981, small transformers and capacitors with PCB levels 500 ppm must be incinerated.

Regulations in 40 CFR Part 761 also covered the areas of PCB containers, spills, testing dielectric oils, storage facilities, labeling, decontamination, leaks and record keeping. Industry was required to check all transformers, capacitors, hydraulic systems, heat exchangers, motors and other potential uses for PCBs, and if present or suspected, take the appropriate steps to insure that all EPA regulations under TSCA were being met.

No one manufactures polychlorinated biphenols in the U.S. anymore. Nor is anyone deliberately adding PCBs to transformer fluids and the like. But PCBs have left a troublesome legacy, nonetheless. An estimated 750 million lb of PCBs, once among the most common ingredients in dielectric fluids, are still extant in old transformers and recycled transformer oil. Environmentalists and businessmen are joining forces to try to assure that the PCB content in their transformer fluids, etc., are not running afoul of the rules.

However, the ability of existing programs to manage the nation's hazardous wastes is being seriously questioned. In an examination of toxic waste management it appears that the present methods are insufficient to assure "consistent nationwide levels of protection" against the potential health effects of hazardous wastes.

The available techniques or methods for handling hazardous wastes and other materials containing PCBs include:

1. Landfills and impoundments
2. Injection wells
3. Incineration and other thermal destruction
4. High temperature decomposition
5. Chemical treatment All of the known methods have some problem(s) areas associated therewith. For example, landfill and injection wells are not effective for liquids, particularly in that leaching occurs with surface and ground water being adversely effected. In the case of incineration and other thermal destruction the cost is high and the air is adversely effected. The chemical methods basically chemical stabilization techniques as practiced heretofore are costly and due to the solubility of either the reactants or reaction products, produce a leachate which adversely affects the ground water.

In accordance with the invention the applicant has found that the problems associated with waste management where polychlorinated biphenyls and other toxic chlorinated compounds for instance ethylene dibromide, can be avoided by treating the material to be decontaminated i.e., sludge, spent catalyst, reactor-distillation residues, fuels, etc., containing PCBs with an alloy of sodium, copper and lead (NaPbCu) at a temperature above the melting point of sodium under intense mixing. Under these conditions the sodium reacts with the chlorine present to form NaCl and CuPb.

The reaction is carried out by first forming the NaPbCu alloy. This is accomplished by reacting a slurry of metallic sodium in oil with a catalytic amount of copper i.e. 1–4%, preferably 1–2% plus an equal or slightly larger amount of lead. The lead is required to be present in an amount sufficient to effect the alloying of the copper and sodium.

Alternatively the Na-Cu-Pb alloy can be prepared by introducing the copper and lead into contact with the sodium under argon at a temperature of about 450° F. The ternary alloy which is formed after cooling is dispersed in oil to form the slurry When it was attempted to form the alloy by first reacting sodium and copper under these conditions no alloy was formed, the two metals remaining separate and distinct.

The slurry of sodium copper lead alloy in oil is contacted with the waste material containing PCBs or ethylene dibromide or other halogenated hydrocarbon, for example a fuel oil at a temperature above the melting point of the sodium i.e., 250°–300° F., under conditions of high agitation with the alloy and more particularly the sodium present in the alloy in excess with respect to the halogen present.

The slurry of alloy must be dispersed throughout the waste material so that intimate contact between the alloy and the PCBs present in the waster material can take place. This is accomplished by violently stirring the alloy into and with the waste material. Under these conditions the sodium and possibly some of the copper reacts rapdily with the chlorine. The sodium forms NaCl. Water can then be added to the waste material or fuel oil for extracting the sodium chloride and destroying any unalloyed sodium present. The sodium, lead and copper which have not reacted with chlorine are filtered off in alloy form. To the same effect the alloy of copper and lead is recovered by filtration.

A contaminated material containing up to 0.5% of PCBs or other chlorinated material on treatment with the Na-Cu-Pb alloy of the invention where the treatment is carried out for several minutes will have the content of BCPs reduced to 5 p/million. If the contacting is carried out for a period of several hours, the BCPs content is further reduced down to 5 parts/billion.

Applicant first attempted to remove chlorine and other halogens by means of an alkali metal (Na or K) alloyed with a metal from the opposite end of the electromotive series as for example with copper, silver, gold or platinum. The problem with these attempts is that the alloying did not take place between the sodium and copper.

The applicant has now surprisingly found that if there is first formed an alloy of sodium and lead i.e., NaPb alloy, and if this binary alloy is further alloyed with copper, an alloy of sodium-lead-copper is formed in which the sodium activated by the copper strips the chlorine from the PCBs by forming sodium chloride.

The alloy is used in the form of a slurry or intimate dispersion thereof in oil. The alloy as a slurry or dispersion in the oil, in an amount wherein the sodium is present in excess with respect to the chlorine to be stripped, is introduced into the waste material containing the PCBs, violently stirred to effect efficient distribution, the temperature maintained at about 250° to about 300° F. and the reaction wherein the chlorine is rapidly reacted with the sodium allowed to take place.

The copper in the alloy increases the activity of the sodium which is basically responsible for the stripping of the chlorine. The lead serves as a bridge for alloying the sodium and copper.

The sodium which has reacted with chlorine is separated off as sodium chloride if necessary, in the form of its aqueous solution.

The lead-copper alloy and any sodium-lead copper alloy still present are present as particulate solids and can be separated off from the stripped waste material by settling or other conventional method. This feature in itself represents an important improvement over the possible use of sodium alone. It is of course recognized that pure sodium is relatively inactive, but accepting that limitation, it is extremely difficult because of the lightness of the sodium dispersion to recover it from the material being treated wherein it remains suspended. In contrast the copper-lead alloy and sodium-copper-lead alloy are relatively heavy and sink to the bottom from where they are easily recovered. This assures that any unreacted sodium, which in accordance with the invention is present as a part of the alloy Na-Pb-Cu can be recovered i.e., separated off from the material being treated. This results in a great number of benefits as for example, the residual sodium does not itself contribute to any waste disposal management problems and in the case where the material is being processed for reuse i.e., fuel oil after separation of the NaCl and solid alloy it is capable of direct use.

The alloy is formed by reacting a slurry of metallic sodium in oil with a catalytic amount (1–4% preferably 1–2%) of metallic copper and an equal or slightly larger amount of lead. The resultant alloy in the form of its slurry in the oil at a temperature of about 250° F. sets up an active cell and in contact with an oil or effluent or other waste material containing PCBs the sodium activated by the copper, the lead serves as a bridge facilitating the alloying of the sodium and copper, strips the chlorine from the PCBs as sodium chloride. The sodium chloride forms where water is not present as a solid and sinks to the bottom from whence it is decanted or filtered, is stripped by washing with water. The Na-Pb-Cu and Pb-Cu both are solids and are removed by decanting or filtering.

The decontaminated material is processed conventionally, no special precautions being necessary. If the decontaminated material is an oil i.e., transformer, hydraulic fuel after decontamination it is directly suitable for reuse for its intended purpose.

While the disclosure has emphasized PCB decontamination, any halogenated compound such as ethylene dibromide, or other halogenated hydrocarbon, can be rendered non-hazardous by the process of the invention.

It is also possible when treating a fairly clear oil i.e., a fuel oil, to pass a slurry of the alloy in intimate counter current contact, at the indicated temperature, to the fuel oil and to effect the stripping to the same degree.

It is also within the scope of the invention to treat a material which is liquid when the reaction is carried out under pressure.

The following example will serve to illustrate the invention but is not to be construed as limitative of the scope thereof.

EXAMPLE

A fuel oil containing 100 ppm of halogen as PCBs was treated in accordance with the following procedure.

An alloy was prepared by reacting a slurry of metallic sodium in a small amount of the fuel oil. The amount of sodium charged was calculated to provide a 25% excess with respect to the chlorine present in the fuel oil to be treated.

A catalytic amount of metallic copper (1-2%) and the same amount of metallic lead (1-2%) were introduced into the oil-sodium slurry. A terniary alloy of Na-Cu and Pb was formed. The resultant slurry of Na-Cu-Pb alloy was introduced into the oil to be treated in an amount whereby the sodium was present in a large excess (25%) with respect to the chlorine content of the PCBs present.

The reaction was completed in less than 5 minutes at a temperature of 250° F.

The chlorine content decreased from 100 ppm to about 1 ppm (99% stripped).

The sodium halide was removed together with the Na-Cu-Pb (unreacted) and the Cu-Pb alloy by decanting. The sodium halide was efficiently separated from the alloy by washing. The oil was recycled for use as a fuel.

What is claimed is:

1. Process for removing halogentated hydrocarbon from a material containing the same which comprises: forming a ternary alloy of sodium, copper and lead by dispersing sodium metal in oil and reacting the same with a catalytic amount of copper and at least the same amount of lead to provide a slurry of said alloy; contacting the material containing the halogenated hydrocarbon with said slurry using an amount of alloy whereby the sodium is present in excess with respect to halogen present; carrying out said contacting at a temperature of about 250°-300° F. under intense mixing and separately recovering the sodium halide, copper-lead and unreacted sodium-copper-lead alloy from the substantially halogen free material.

2. Process according to claim 1, wherein said halogenated hydrocarbon is a chlorinated or brominated hydrocarbon.

3. Process according to claim 1, wherein said halogenated hydrocarbon is ethylene dibromide.

4. Process according to claim 1 wherein said halogenated hydrocarbon is PCBs.

5. Process according to claim 1, wherein said material containing said halogenated hydrocarbon is a member selected from the group consisting of fuels, textile dyes, printing inks, paints, fireproofing agents, electrical capacitor and transformer fluids, heat exchanger fluids, hazardous wastes and toxic wastes.

6. Process according to claim 1, wherein said material is a liquid fuel.

7. Process according to claim 1 wherein said material is a liquid and said sodium halide is recovered by filtration.

8. Process according to claim 1, wherein said material is a thickened liquid or sludge and said sodium halide is recovered by extraction with water.

9. Process for removing PCBs from a hazardous waste material containing the same which comprises: forming a ternary alloy of sodium, copper and lead by dispersing sodium metal in oil and reacting the same with a catalytic amount of copper and at least the same amount of lead to provide a slurry of said alloy; contacting the hazardous waste material containing the PCBs with said slurry using an amount of alloy whereby the sodium is present in excess with respect to chlorine present; carrying out said contacting at a temperature of about 250°-300° F. under intense mixing and separately recovering the sodium chloride, copper-lead and unreacted sodium-copper-lead alloy from the substantially chlorine free material.

* * * * *